United States Patent [19]

Schlager

[11] Patent Number: 4,913,901

[45] Date of Patent: Apr. 3, 1990

[54] PHARMACEUTICAL COMPOSITION FOR ORAL ADMINISTRATION AND PROCESS FOR THE USE THEREOF

[76] Inventor: Ludwig H. Schlager, Nottebohmstrasse 12, 1190 Vienna, Austria

[21] Appl. No.: 594,060

[22] Filed: Mar. 28, 1984

Related U.S. Application Data

[63] Continuation of Ser. No. 162,997, Jun. 25, 1980, abandoned.

[30] Foreign Application Priority Data

Jun. 25, 1979 [AT] Austria .................. 4449/79
Apr. 24, 1980 [AT] Austria .................. 2210/80

[51] Int. Cl.$^4$ ............... A61K 31/35; A61K 31/74
[52] U.S. Cl. ..................... 424/78; 514/455; 514/962
[58] Field of Search ............. 424/78; 514/455

[56] References Cited

U.S. PATENT DOCUMENTS 4,130,568  12/1978  Confolone et al. ............. 424/263 X
4,454,152   6/1984  Barry et al. .................... 424/283

OTHER PUBLICATIONS

Merck Index, 9th Ed., par. 3246, 4319, 4323, 7349, 7350, 7644 & 5861 (1976).

Primary Examiner—Leonard Schenkman

[57] ABSTRACT

An orally administrable and stable solution containing as an active ingredient Methoxasalen (8-methoxyfuro-[3',-2':6,7]-coumarin) of the formula

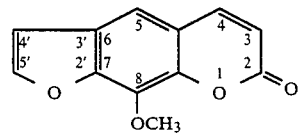

useful in the photochemotherapy of psoriasis, to a process for the preparation thereof and to a process for the use thereof.

25 Claims, 1 Drawing Sheet

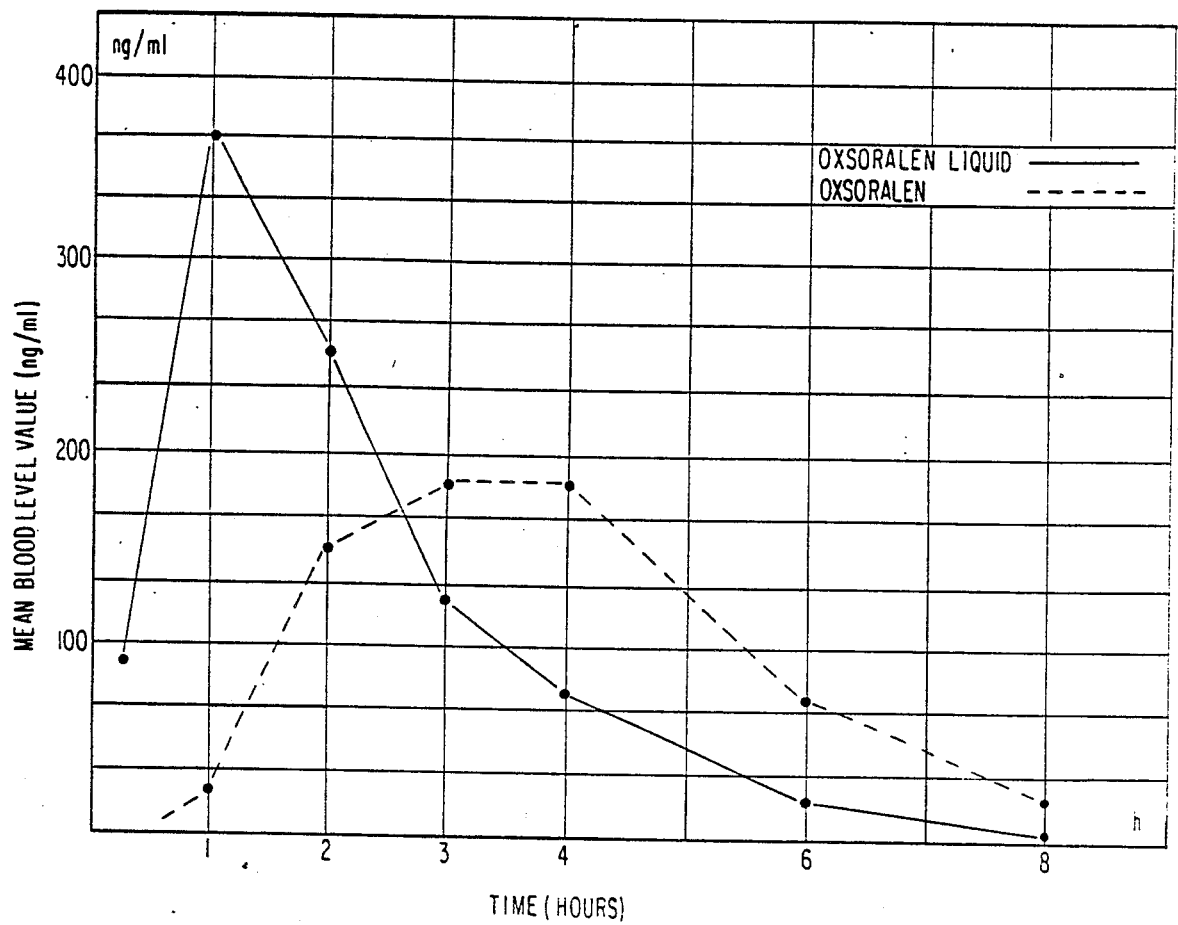

PHARMACEUTICAL COMPOSITION FOR ORAL ADMINISTRATION AND PROCESS FOR THE USE THEREOF

This is a continuation, of application Ser. No. 162,997, filed June 25, 1980.

BACKGROUND OF THE INVENTION

1. Field of the Invention

The present invention relates to an orally administrable and stable solution containing as an active ingredient Methoxsalen (8-methoxyfuro-[3,,2, 6,7]-coumarin) of the formula

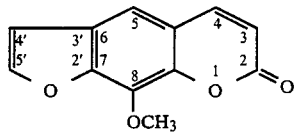

useful in the photochemotherapy of psoriasis, to a process for the preparation thereof and to a process for the use thereof.

2. Background of the Invention

In the oral application of Methoxsalen in solid form, usually up to now (as tablets or capsules containing the powdery active ingredient) the patient ma be subjected to irradiation only after two hours after administration of the medicament (*Wien.Klin.Wschr.*, 89, Suppl. 75 (1977)), which fact is complicated and time-consuming both for the physician and for the patient. Furthermore, levels of Methoxsalen of different height appear in the patient's blood, so that the optimum duration of the irradiation varies between single treatments even with the same patient. Therefore, there is a demand for a form of administration which enables the blood level of Methoxsalen required for the irradiation to be available within a shorter period of time and at a height substantially equal each time. Up to now no adequate preparation has been available to achieve this.

Methoxsalen is a substance which is soluble in most solvents to a small extent. It is quite soluble in chloroform and in aqueous alkali, but these two solvents cannot be used for the preparation of a solution suitable for oral administration which can be filled into capsules Furthermore, an alkaline medium results in the cleavage of the coumarin ring. If Methoxsalen is dissolved in a pharmaceutically useful, but aqueous solvent, frequently a yellow coloring develops during storage. Additionally, in case of a higher content of water a precipitate is formed. Further some anhydrous solvents can not be employed without irritations due to their hygroscopic properties.

SUMMARY OF THE INVENTION

It has been found that the preparation of a stable solution of Methoxsalen suitable for oral administration may be achieved by using a specific solvent system for Methoxsalen.

Accordingly in one embodiment, this invention provides a stable pharmaceutical preparation for treatment of psoriasis comprising a solution of (a) Methoxsalen and (b) a solvent selected from the group consisting of (1) a polyethylene glycol or an ether or ester thereof; (2) a derivative of 1,3-dioxolane; (3) an alkylene glycol; (4) a pharmaceutically acceptable ethereal oil; (5) an ester or partial ester of a $C_2$ to $C_{30}$-fatty acid with a 2- to 8-valent alcohol or with a polyglycerol; (6) a dialkylamide having 3 to 6 carbon atoms, (7) dimethyl sulfoxide and (8) a mixture thereof and, optionally, additionally with water and/or alcohols.

In another embodiment this invention provides a process for preparing an orally-effective stable solution of Methoxsalen comprising dissolving Methoxsalen in a solvent selected from the group consisting of (1) a polyethylene glycol or an ether or ester thereof; (2) a derivative of 1,3-dioxolane; (3) an alkylene glycol; (4) a pharmaceutically acceptable ethereal oil; (5) an ester or partial ester of a $C_2$ to $C_{30}$-fatty acid with a 2- to 8-valent alcohol or with a polyglycerol; (6) a dialkylamide having 3 to 6 carbon atoms, (7) dimethyl sulfoxide and (8) a mixture thereof and, optionally, additionally with water and/or alcohols.

In an even further embodiment, this invention provides a process for treating a patient affected with psoriasis comprising orally administering a stable solution comprising (a) a therapeutically effective amount of Methoxsalen dissolved in (b) a solvent selected from the group consisting of (1) a polyethylene glycol or an ether or ester thereof; (2) a derivative of 1,3-dioxolane; (3) an alkylene glycol; (4) a pharmaceutically acceptable ethereal oil; (5) an ester or partial ester of a $C_2$ to $C_{30}$-fatty acid with a 2- to 8-valent alcohol or with a polyglycerol; (6) a dialkylamide having 3 to 6 carbon atoms, (7) dimethyl sulfoxide and (8) a mixture thereof and, optionally, additionally with water and/or alcohols and then irradiating the patient with ultraviolet light.

BRIEF DESCRIPTION OF THE ACCOMPANYING DRAWING

The accompanying figure shows the mean values of levels of Methoxsalen in the blood with respect to time in hours, comparing the liquid form pharmaceutical preparation of this invention (OXSORALEN liquid) with the solid form preparation (OXSORALEN) for comparison.

DETAILED DESCRIPTION OF THE INVENTION

If the solutions of this invention are administered orally, one hour later the maximum level of Methoxsalen in the blood is achieved. Additionally if some solutions are cooled to +4° C., no crystallization of the Methoxsalen active ingredient results, so that cold storage of some solution is possible.

For convenience in administration, capsules generally contain a predetermined amount of the active ingredient (e.g., 10 mg), and in case of this form of administration, this amount or a multiple thereof is available as the dosage. In order to be able to comply with a more individual dosage, especially in the case of UVA-sensitive (UVA is ultraviolet light in the range of 320 to 390 nanometers) type of skin, it is desirable to have available also a solution which can be administered dropwise; adjusted to, e.g., a content of 1 mg of the active ingredient per drop, so that any desired dosage can be obtained. These concentrations are not limiting, however, and a suitable concentration for the active ingredient in the solution of this invention can range from 5 to 50 mg per capsule for capsule administration and from 0.5 to 5 mg per drop for dropwise administration. A suitable dosage amount of the Methoxsalen which can be employed is 5 to 10 mg for a body weight of up to 30 kg, 10 to 60 mg for a body weight of 30 to 90 kg and 60 to 70 mg for a body weight above 90 kg.

In the case of solutions of this invention, particularly suitable solvents which can be used for solutions for filling capsules include polyethylene glycol or an ether or ester thereof, a derivative of 1,3-dioxolane, an alkylene glycol and a mixture thereof, optionally, additionally with water and/or alcohols.

Suitable polyethylene glycols which can be used in the solutions of this invention are polyethylene glycols having a molecular weight ranging from about 200 to about 2000. Further, an ether or an ester of such a polyethylene glycol can be used and suitable examples are polyethylene glycol ethers and esters wherein the ether or the ester moiety contains from 2 to 30 carbon atoms. Suitable examples of alcohols which be etherified and acids which can be esterified with the polyethylene glycol include fatty alcohols and fatty acids having, as described above, 2 to 30 carbon atoms.

Suitable derivatives of 1,3-dioxolane which can be used are cyclic acetals of polyhydric alcohols, for example, glycerol.

Suitable examples of alkylene glycols which can be used are those having 3 to 6 carbon atoms, for example, propylene glycol, butylene glycol, sorbitol, etc.

In case of a solution to be administered dropwise, in addition to viscosity and surface tension characteristics also the quality of the solution as regards taste should be considered. It has been found that particularly suitable solvents which can be used in preparing solutions for dropwise administration include ethereal oils, fatty acid esters or partial fatty acid esters of polyhydric alcohols, lower molecular weight dialkylamides or dimethyl sulfoxide and mixtures of these solvents are suitable for the preparation of standardized and stable solutions of Methoxsalen which can be administered dropwise. Suitable examples of these materials which can be used are described hereinafter in the Examples of this invention. These solutions to be administered dropwise may contain, if desired, also taste corrigents, antioxidants and preservatives. As a result, cold storage is not necessary.

As described above, water and/or alcohols can be employed optionally in admixture with the above-described solvents. A suitable amount of water which can be used is up to 30% by volume of the total solvent used and a suitable amount of alcohol which can be used is up to 70% by volume of the total solvent used. Suitable examples of alcohols which can be optionally used in the solutions of this invention include alcohols having 2 to 7 carbon atoms, for example, ethanol, propanol, benzyl alcohol, etc.

Furthermore, the use of mixtures of the above mentioned solvents may be advantageous.

The following examples are given to illustrate the present invention in greater detail. Unless otherwise indicated, all parts, percents, ratios and the like are by weight.

EXAMPLE 1

1 g of Methoxsalen was dissolved with stirring and heating at 60° C. in a mixture of 20 ml of 1,2-propylene glycol, 30 ml of glycofurol and 30 ml of polyethylene glycol 400. After cooling to 20° C. it was diluted with distilled water to a total volume of 100 ml. The mixture which had become warm was cooled again to 20° C., it was diluted again with distilled water to a total volume of 100 ml, shaken thoroughly, and then filtered. Capsules were then filled with the solution using a metering device.

EXAMPLE 2

A suspension of 6 g of microfinely powdered Methoxsalen in 90 ml of glycofurol was heated on a water bath with stirring until a clear solution was obtained. After cooling to 20° C. the solution was diluted with glycofurol to a volume of 100 ml and shaken thoroughly Then the solution was further processed as described in Example 1.

EXAMPLE 3

10 g of microfinely powdered Methoxsalen was dissolved by stirring in a mixture of 485 g of polyethylene glycol 400, 15 g of 1,2-propylene glycol and 15 g of glycerol, diluted with 15 g of water, and stirred thoroughly. Capsules were then filled with the obtained solution using a metering device, 540 mg per capsule. These capsules contained as a result 10 mg of the active ingredient per capsule.

EXAMPLE 4

0.43 g of Methoxsalen was dissolved with stirring and heating at 60° C. in a mixture of 7.46 of glycerol triacetate, 1.9 g of N,N-dimethylacetamide and 1.0 g of polyoxyethylene (20)-sorbitan monooleate. After cooling to 20° C. 0.04 g of a flavoring substance was added and the obtained mixture (10 ml) was stirred, until homogenity was achieved. 1 ml thereof provided from a calibrated pipette 43 drops, i.e. 1 drop contained 1 mg of the active ingredient.

EXAMPLE 5

0.44 g of Methoxsalen was dissolved with stirring and heating at 50° C. in a mixture of 5.12 of glycerol triacetate, 2.28 g of N,N-dimethylacetamide, 1.9 g of peppermint oil and 0.64 g of polyoxyethylene (20)-sorbitan monooleate. After cooling the mixture to room temperature, 10 ml of a mixture was obtained which provided from a calibrated pipette 44 drops/ml. Therefore, 1 drop contained 1 mg of the active ingredient.

By repeating the procedures of Examples 4 and 5 above, solutions as described below were obtained, which each contained 1 mg of the active ingredient per drop:

EXAMPLE 6

0.34 g of Methoxsalen
6.50 g of polyethylene glycol 300
1.80 g of a mixture of partial esters cf $C_8$-$C_{12}$ fatty acids with oxyethylated glycerol
1.06 g of benzyl alcohol
0.92 g of glycerolformal
5 0.16 g of flavoring agent

EXAMPLE 7

0.42 of Methoxsalen
4.80 g of glycerolformal
2.20 g of glycofurol
1.84 g of peppermint oil
1.56 g of a mixture of partial esters of hydrogenated castor oil fatty acids with oxyethylated glycerol

EXAMPLE 8

0.43 g of Methoxsalen
5.00 g of glycerolformal
2.32 g of polyethylene glycol 300

2.06 of a mixture of partial esters of castor oil fatty acids with oxyethylated glycerol
1.34 g of dimethyl sulfoxide
0.16 g of flavoring agent

EXAMPLE 9

10 g of powdered Methoxsalen was dissolved by stirring a mixture of 365 g of polyethylene glycol 400, 50 g of dimethylacetamide, 50 g of glycerol and 40 g of glycerol triacetate, diluted with 30 g of water, and stirred thoroughly. Capsules were then filled with the obtained solution using a metering device, 0.5 ml per capsule. Each of these capsules contained 10 mg of the active ingredient.

The comparative bioavailability of conventional Methoxsalen preparations and the comparative bioavailability of the solutions of this invention in human beings are described below.

1. TEST PROCEDURE

1.1 Test Persons

Seven patients suffering from psoriasis voluntarily took part in the test. Before performing the test the patients were informed about the performance and purpose of the examination and all patients agreed to the course of and performance of the examination.

Additionally the patients were subjected to a careful medical examination and to a blood-urine test. The laboratory values obtained after examination did not differ in any extent to those obtained before the examination.

1.2 Test Materials (a) Methoxsalen solution of this invention in capsules, hereinafter OXSORALEN LIQUID capsules, Gerot, 10 mg Methoxsalen/capsule, prepared according to Example 3.

(b) Comparison material in capsule form, hereinafter OXSORALEN capsules, Gerot, 10 mg Methoxsalen/capsule, containing the active ingredient Methoxsalen in powder form together with 99 mg of lactose, 30 mg of corn starch, 1.5 mg of gelatin, 4.5 mg of magnesium stearate and 4.5 mg of talcum.

The term Gerot above refers to Gerot-Pharmazeuteka Gessellschaft m.b.H.

1.3 Dosage

The dosage of the two medicaments was effected in a crossover-arrangement on two different examination days with an interval of one week as a washing out phase. On the examination days the patients each received 4 capsules of OXSORALEN LIQUID resp. each 4 capsules of OXSORALEN in the morning on an empty stomach.

1.4 Drawing of Blood

After a value of zero, further blood was drawn from all patients on both examination days at the following times:
1, 2, 3, 4, 6, 8 and 24 hours.

The serum was recovered from the blood, deepfrozen and maintained so up to the time of analysis.

1.5 Analysis of the Serum

The serum was analyzed according to a HPLC method developed in the research laboratory of GEROT.

2. Results

The mean values of the results of the analysis of the serum are shown in the accompanying drawing

3. Discussion

Both my experience and also numerous literature references indicate a large degree of biological scattering range after administration of Methoxsalen in crystalline form in capsules or tablets. This inconstant resorption particularly occurs in case of the PUVA-treatment (psoralene therapy with UVA light) to a very great disadvantage.

A second disadvantage is the long delay after administration of the preparation until irradiation. With prior art forms of oral administration, this delay before irradiation amounts to 2 to 3 hours.

Both of the above-described disadvantages can be removed by the new OXSORALEN LIQUID-capsule in which the Methoxsalen is available to the organism in form of the solution of this invention.

Not only can the maximum serum concentration be achieved within one hour (an exact examination of the patients showed that the maximum serum concentration definitely correlated with the maximum clinical reaction of the patients), but also substantially more constant and higher serum concentrations can be achieved after administration of OXSORALEN LIQUID.

A direct comparison of the two areas below the blood level curves shown in the figure demonstrates that OXSORALEN LIQUID administered in capsules is resorbed better by the factor 1.25 than OXSORALEN in the usual formulation.

As described above, the solutions of this invention are advantageously effective in the treatment of psoriasis in combination with irradiation with UV light. This treatment technique is well known in the art and is described in, e.g., Wiener, *Klinische Wochenschrift,* Supp. 75, 1977, F. Gschnait, "Orale Photochemotherapie".

While the invention has been described in detail and with reference to specific embodiments thereof, it will be apparent to one skilled in the art that various changes and modifications can be made therein without departing from the spirit and scope thereof.

What is claimed is:

1. An orally administrable pharmaceutical preparation for treatment of psoriasis comprising a stable solution of (a) at least 1.0% by weight of 8-methoxy-furo [3',2':6,7]-coumarin as an active ingredient; (b) a polyethylene glycol or an ether or ester thereof; and optionally (c) a solvent selected from the group consisting of (1) a derivative of 1,3-dioxolane; (2) an alkylene glycol; (3) a pharmaceutically acceptable ethereal oil; (4) an ester or partial ester of a $C_2$ to $C_{30}$-fatty acid with a 2- to 8-valent alcohol or with a polyglycerol; (5) a dialkylamide having 3 to 6 carbon atoms; (6) dimethyl sulfoxide and (7) a mixture thereof.

2. The preparation of claim 1, in which said solvent is a partial ester of a $C_2$ to $C_{30}$-fatty acid with a 2-valent to 8-valent alcohol in which the alcohol is etherified at any unesterified OH-groups with polyethylene glycol.

3. The preparation of claim 1, in which said solvent is an ester or partial ester of a fatty acid which is unsaturated and/or contains an OH group.

4. The preparation of claim 1, additionally containing one or more of a pharmaceutically acceptable flavoring agent, a pharmaceutically acceptable antioxidant and a pharmaceutically acceptable preservative.

5. The preparation of claim 1, additionally containing water, an alcohol or a mixture thereof.

6. The preparation of claim 1, in a capsule form.

7. The preparation of claim 1, wherein said 8-methoxy-furo [3',2':6,7]-coumarin is present in an amount of from 1.0 to 6.0% by weight.

8. An oral dosage composition in a unit dosage form comprising a solution of an amount of methoxsalen effective for the treatment of psoriasis in polyethylene glycol or a mixture of polyethylene glycols within a capsule.

9. An oral dosage composition in unit dosage form comprising a solution, which in percent by weight based on the total weight of the composition is at least 1% of methoxsalen and 99% or less of polyethylene glycol or a mixture of polyethylene glycols contained within a capsule.

10. An oral dosage composition in unit dosage from comprising a solution, which in percent by weight based on the total weight of the composition is 1% to 6% of methoxsalen and 99–94% or polyethylene glycol or a mixture of polyethylene glycols contained within a capsule.

11. An oral dosage composition in a unit dosage form comprising a solution of an amount of methoxsalen effective for the treatment of psoriasis in about 31.4 to about 89.9 percent by weight of the composition of a polyethylene glycol which is fluid at room temperature, contained within a capsule.

12. An orally administrable pharmaceutical preparation for treatment of psoriasis comprising a stable solution of (a) at least 0.9% by weight of 8-methoxy-furo [3',2':6,7]-coumarin as an active ingredient; (b) a polyethylent glycol or an ether or ester thereof; and optionally (c) a solvent selected from the group consisting of (1) a derivative of 1,3-dioxolane; (2) and alkylene glycol; (3) a pharmaceutically acceptable etheral oil; (4) an ester or partial ester of a $C_2$ to $C_{30}$-fatty acid with a 2- to 8-valent alcohol or with a polyglycerol; (5) a dialkylamide having 3 to 6 carbon atoms; (6) dimethyl sulfoxide and (7) a mixture thereof.

13. The preparation of claim 12, wherein said 8-methoxy-furo [3',2':6,7]-coumarin is present in an amount of from 0.9 to 5.6% by weight.

14. An oral dosage composition in a unit dosage form comprising a solution of an amount of methoxsalen effective for the treatment of psoriasis in about 30 to about 90 percent by weight of the composition of a polyethylene glycol which is fluid at room temperature, contained within a capsule.

15. A process for treating a patient afflicted with psoriasis comprising
orally administering a stable solution comprising (a) at least 1.0% by weight of 8-methoxy-furo [3',2':6,7]-coumarin dissolved in (b) a polyethylene glycol or an ether or ester thereof; and optionally (c) a solvent selected from the group consisting of (1) a derivative of 1,3-dioxolane; (2) an alkylene glycol; (3) a pharmaceutically acceptable ethereal oil; (4) an ester or partial ester of a $C_2$ to $C_{10}$-fatty acid with a 2- to 8-valent alcohol or with a polyglycerol; (5) a dialkylamide having 3 to 6 carbon atoms; (6) dimethyl sulfoxide and (7) mixtures thereof, and irradiating the patient with ultraviolet light.

16. The process of claim 15, in which said solvent is a partial ester of a $C_2$ to $C_{30}$-fatty acid with a 2-valent to 8-valent alcohol in which the alcohol is estherified at any unesterified OH-groups with polyethylene glycol.

17. The process of claim 15, in which said solvent is an ester or partial ester of a fatty acid which is unsaturated and/or contains an OH group.

18. The process of claim 15, additionally containing one or more of a pharmaceutically acceptable flavoring agent, a pharmaceutically acceptable antioxidant and a pharmaceutically acceptable preservative.

19. The process of claim 15, additionally containing water, an alcohol or mixture thereof.

20. The process of claim 15, wherein said 8-methoxy-furo [3',2':6,7]-coumarin is present in an amount of from 1.0 to 6.0% by weight.

21. A method of treating a subject afflicted with psoriasis which method comprises:
(a) administering to the subject an oral dosage composition comprising a solution of an amount of methoxsalen effective for the treatment of psoriasis in polyethylene glycol or a mixture of polyethylene glycols within a capsule;
(b) waiting a sufficient time to obtain a peak blood level of methoxsalen in the subject; and
(c) irradiating the subject with ultraviolet light.

22. A method of treating a subject afflicted with psoriasis which method comprises:
(a) administering to the subject an oral dosage composition comprising a solution of an amount of methoxysalen effective for the treatment of psoriasis in about 30 to about 90 percent by weight, based upon the total weight of the composition, of a polyethylene glycol which is a fluid at room temperature, contained within a capsule.
(b) waiting a sufficient time to obtain a peak blood level of methoxsalen in the subject; and
(c) irradiating the subject with ultraviolet light.

23. A method of treating a subject afflicted with psoriasis which method comprises:
(a) administering to the subject an oral dosage composition comprising a solution of an amount of methoxsalen effective for the treatment of psoriasis in about 31.6 to about 89.8 percent by weight, based upon the total weight of the composition, of a polyethylene glycol which is fluid at room temperature, contained within a capsule.
(b) waiting a sufficient time to obtain a peak blood level of methoxsalen in the subject; and
(c) irradiating the subject with ultraviolet light.

24. A process for treating a patient afflicted with psoriasis comprising
orally administering a stable solution comprising (a) at least 0.9% by weight of 8-methoxy-furo [3',2':6,7]-coumarin dissolved in (b) a polyethylene glycol on an ether or ester thereof and optionally (c) a solvent selected from the group consisting of (1) a derivative of 1,3-dioxolane; (2) an alkylene glycol; (3) a pharmaceutically acceptable ethereal oil; (4) an ester or partial ester of a $C_2$ to $C_{10}$-fatty acid with a 2- to 8-valent alcohol or with a polyglycerol; (5) a dialkylamide having 3 to 6 carbon atoms; (6) dimethyl sulfoxide and (7) mixtures thereof, and irradiating the patient with ultraviolet light.

25. The process of claim 24, wherein said methoxyfuro [3',2':6,7]-coumarin is present in an amount of from 0.9 to 5.6% by weight.

* * * * *